United States Patent
Leclercq et al.

(10) Patent No.: US 6,558,427 B2
(45) Date of Patent: May 6, 2003

(54) KNEE IMPLANT

(75) Inventors: Vincent Leclercq, Winterthur (CH); Bernhard Gyssler, Horgen (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/866,218

(22) Filed: May 25, 2001

(65) Prior Publication Data

US 2001/0047211 A1 Nov. 29, 2001

(30) Foreign Application Priority Data

May 29, 2000 (EP) ............................................. 00810467

(51) Int. Cl.$^7$ ................................................. A61F 2/38
(52) U.S. Cl. .............................. 623/20.33; 623/20.32; 623/20.31; 623/20.14; 623/20.15
(58) Field of Search .................... 623/20.32–20.34, 623/20.14–20.15, 20.21–20.31

(56) References Cited

U.S. PATENT DOCUMENTS 5,282,868 A * 2/1994 Bahler ..................... 623/20.29
5,395,401 A    3/1995 Bahler
5,413,604 A    5/1995 Hodge
5,871,543 A    2/1999 Hofmann
6,013,103 A    1/2000 Kaufman

FOREIGN PATENT DOCUMENTS

EP    0634156 A2    1/1995
GB    2 278 782 A   12/1994

* cited by examiner

Primary Examiner—David J. Isabella
Assistant Examiner—Urmi Chattopadhyay
(74) Attorney, Agent, or Firm—Townsend and Townsend and Crew LLP

(57) ABSTRACT

A knee prosthesis has a medial condyle (1) and a lateral condyle (5), the running surfaces (2) of which and the counter-surfaces A, B of which that lie on a tibia platform (3) are sections of spherical surfaces with radii $R_1$, $R_2$, with their center $M_1'$ and $M_2'$ forming in their vertical projection onto the counter-surfaces A, B the points $M_1$, $M_2$. The lateral counter-surface B belongs to a lateral meniscus part (7) which, guided on a plane (13) of the tibia platform, is pivotal with the point $M_2$ on a circular arc with radius $R_3$ about the point $M_1$, with the radius $R_3$ corresponding to the distance a of the centers $M_1'$, $M_2'$.

11 Claims, 3 Drawing Sheets

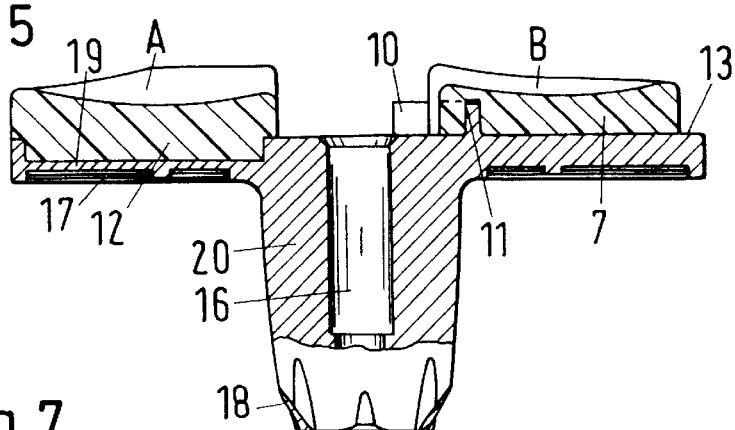
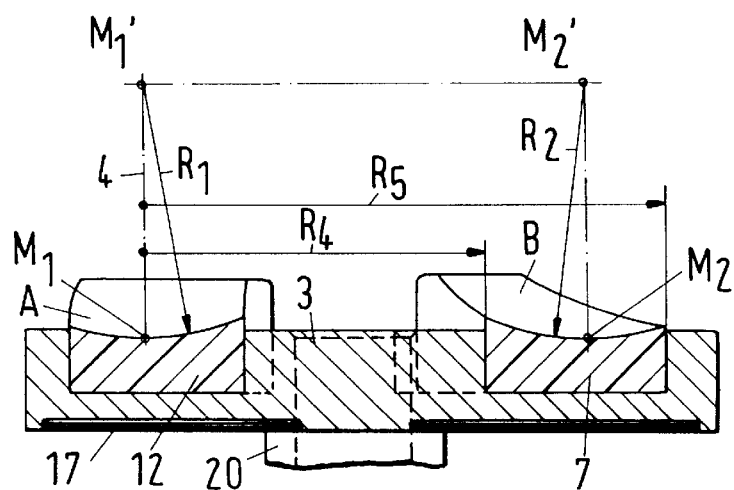
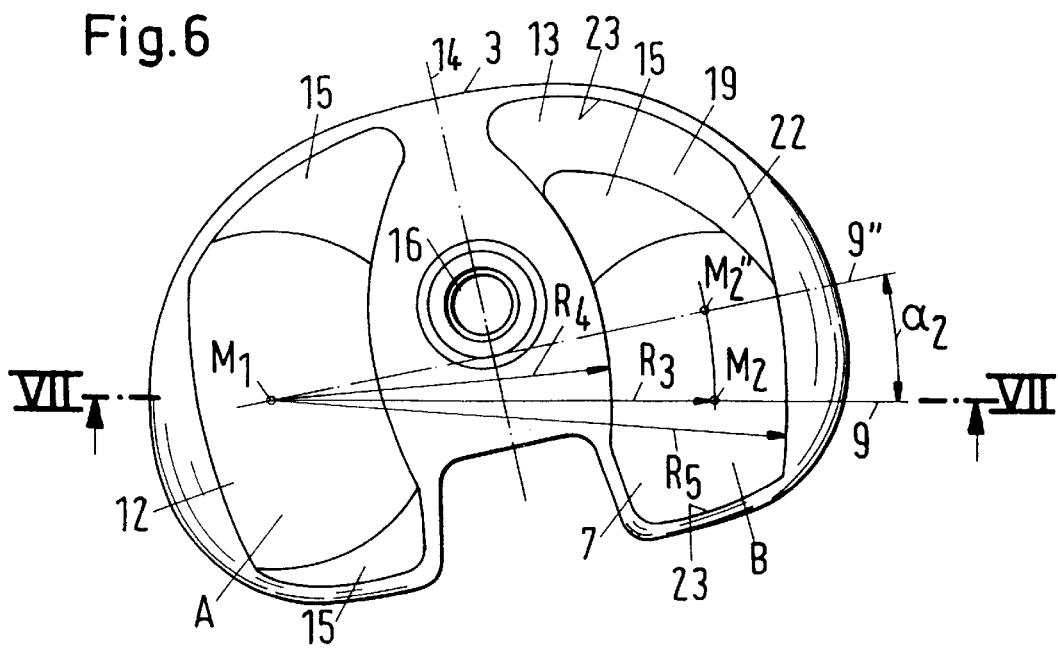

KNEE IMPLANT

BACKGROUND OF THE INVENTION

The invention relates to a knee prosthesis comprising a medial condyle, the running surface of which and the counter-surface A of which that lies on a tibia platform are sections of spherical surfaces with a radius $R_1$, the center $M_1'$ of which forms in its vertical projection onto the counter-surface A an axis with a point $M_1$ about which a lateral condyle is pivotal.

A knee prosthesis is shown in the patent specification U.S. Pat. No. 5,219,362 in which a large contact surface exists on the medial side between the medial condyle and the oppositely lying tibia platform. In the lateral condyle there is at most a linear contact during the flexion, which leads to undesirably high area pressings.

SUMMARY OF THE INVENTION

It is an object of the invention to improve this situation. This is achieved in that the lateral condyle with its running surface and its counter-surface B are likewise sections of spherical surfaces with a radius $R_2$ with center $M_2'$, the vertical projection of which onto the counter-surface B corresponds to a point $M_2$; and in that the counter-surface B belongs to an artificial meniscus part which can be displaced on a plane of the tibia platform and which, guided on a circular arc, is pivotal with the point $M_2$ about the point $M_1$ at a distance $R_3$ which corresponds to the distance a of the centers $M_1'$, $M_2'$.

This arrangement prevents large surface pressings and allows the tibia a rotational movement of the tibia platform about a point $M_2$ on its medial counter-surface A during the flexion corresponding to the attached ligaments and, with the rotational movement, a movement of the lateral side of the tibia platform towards the anterior, whereas the meniscus part of the lateral side remains in place relative to the lateral condyle.

The tibia platform is pivotal from a middle position which corresponds to the extension position and in which the points $M_1$, $M_1'$, $M_2$, $M_2'$ lie in a transversal plane of the tibia platform by an angle $\alpha_1 \geq 0$ towards the posterior into a position which corresponds to the hyperextension and in the event of complete flexion by an angle $\alpha_2$ between 5° and 20° towards the anterior. Furthermore, it can be advantageous to limit the sum of the angles $\alpha_1$ and $\alpha_2$ to a value between 12° and 18° in order constructionally to achieve a larger counter-surface B for the lateral condyles.

A circular-arc-shaped bulge of the tibia platform, which projects over a sliding plane for the meniscus part and, engages into a groove of the meniscus part for the guiding about the point $M_1$, has the advantage that no foreign objects can collect and be squashed on the sliding plane or in the groove since they are always brushed off again through the relative movement between the meniscus part and the tibia platform. This presupposes that no larger shoulders, but rather at most end abutments for the movement, project above the sliding plane in the direction of movement.

The tibia platform itself can however also be provided on the lateral side with a wide circular groove, the limiting radii of which have the common center $M_1$ on the medial side; and the meniscus part is designed as a part of a circular ring which is guided by the groove.

Through the spherical contact surface on the medial side and through the spherical contact surface of the lateral meniscus part, which is planar on the lower side, the surface pressing can be lowered to such an extent that a plastic body is inserted medially on the tibia platform and that a plastic body is inserted as meniscus part, both for example of high molecular polyethylene.

The use of plastic bodies medially and laterally has the advantage that the tibia platform can be made symmetrical with respect to its sagittal plane and that the tibia platform can be inserted selectively for a left or right knee in that the medial plastic body can be firmly anchored and the lateral meniscus part is pivotal with its point $M_1$ on a radius $R_3$ about the point $M_1$ of the medial side.

In the following the invention will be explained with reference to exemplary embodiments.

BRIEF DESCRIPTION OF THE DRAWINGS

FIG. 5 is a section through a tibia platform as in FIG. 4 with plastic bodies;

FIG. 6 is a plan view of a symmetrical tibia platform which is equipped with plastic bodies for a right knee; and FIG. 7 is a section taken along line VII—VII of FIG. 6.

DESCRIPTION OF THE PREFERRED EMBODIMENTS

Figure 1:
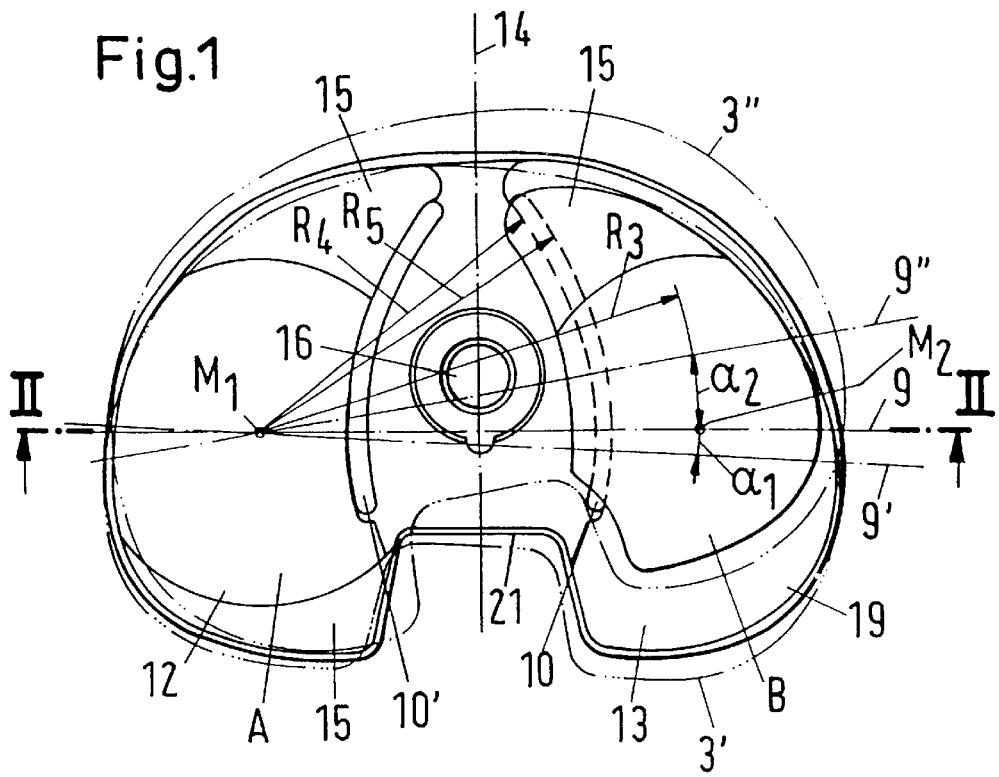
FIG. 1 is a plan view of a tibia platform of a right knee with a firmly anchored plastic part on the medial side and a movable meniscus part of plastic on the lateral side.

The figures show a knee prosthesis comprising a medial condyle 1 and a lateral condyle 5, the running surfaces 2 of which and the counter-surfaces A, B of which that lie on a tibia platform 3 are sections of spherical surfaces with radii $R_1$, $R_2$, with their centers $M_1'$, $M_2'$ forming in their vertical projection onto the counter-surface A, B the points $M_1$, $M_2$. The lateral counter-surface B belongs to a lateral meniscus part 7 which, guided on a plane 13 of the tibia platform, is pivotal with the point $M_2$ on a circular arc with radius $R_3$ about the point $M_1$, with the radius $R_3$ corresponding to the distance a of the centers $M_1'$, $M_2'$.

In the following, identical reference symbols will be used for identical functions.

Figure 2:
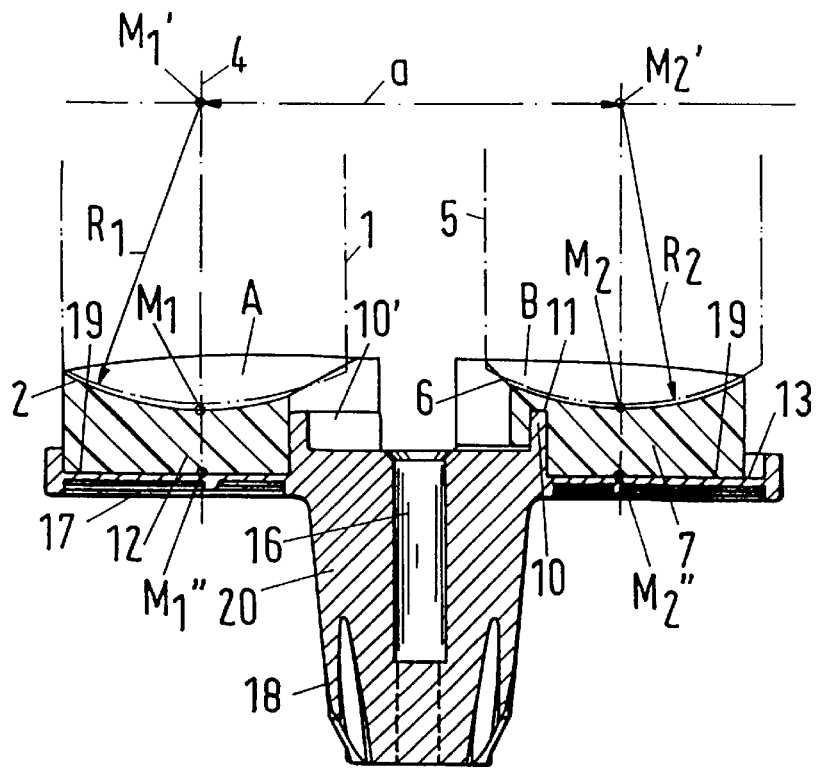
FIG. 2 is a section of FIG. 1 in a transversal plane in which the condyles of the knee joint are also indicated.
Figure 3:
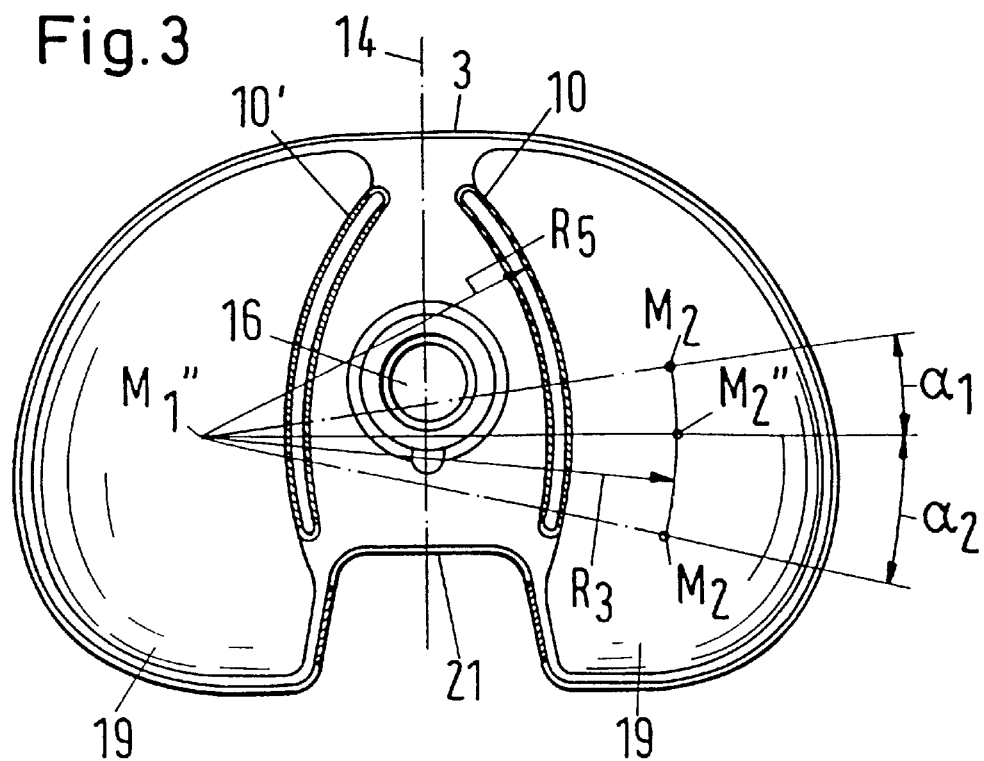
FIG. 3 is, without showing the plastic part, a plan view of the tibia platform of FIG. 1 with depressions and guiding bulges which are symmetrical with respect to the sagittal plane.

In the example of FIGS. 1, 2 and 3 the tibia platform 3 is made symmetrical with respect to its sagittal midplane 14, has towards the distal a spigot 20 with ribs 18 and a central bore 16 and is provided on its upper side medially and laterally in each case with a planar 13 depression 19. Towards the middle the depression is in each case closed off by a circular bulge 10, 10' with bounding radii $R_4$ and $R_5$. Posteriorly a recess 21 for the rear cruciate ligament is present. On the lower side a coating 17 for the better anchoring in the bone or in bone cement is provided. This coating can for example be metal grids.

If a platform 3 is made symmetrical as shown in FIGS. 1 and 6, each side is selectively suitable for the reception of a firmly anchorable plastic body 12 or of a movable meniscus part 7 in order to produce right and left tibia joint halves with one tibia platform.

In FIG. 2 two condyles 1, 5 of the femur side are indicated with phantom lines. The condyles 1, 5 and their counter-surfaces A, B on the tibia platform 3 are sections of spherical surfaces with radii $R_1$, $R_2$ and centers $M_1'$, $M_2'$. The condyles rotate during the flexion about a straight connection line of the centers $M_1'$, $M_2'$, which have a distance "a" with respect to one another. In the medial depression 19 a plastic body 12 is fixed which completely fills out the depression 19. In the lateral depression 19 an artificial meniscus part 7 of plastic is inserted which can slide on the plane 13 and which is guided by a groove 11 at the lateral bulge 10. With a vertical projection of the centers $M_1'$ and $M_2'$ the points $M_1$, $M_2$ arise on the counter-surfaces and the points $M_1''$ and $M_2''$ at the tibia platform 3 on the planes 13. The running surface 2 of the medial condyle 1 and the running surface 6 of the lateral condyle 5 project laterally somewhat. The meniscus part 7 is pivotal about the point $M_1$ and about a vertical straight line $M_1'$, $M_1$ forming an axis 4.

In FIG. 1 the tibia platform 3 is illustrated in an extension position of the (non-illustrated) condyles in which the points $M_1$ and $M_2$ lie in a transversal plane 9 of the tibia platform 3. The condyles 1, 5 lie in each case on the counter-surfaces A, B. From this middle position the condyles can continue to rotate into a hyperextension position. At the same time ligaments at the tibia produce a torque which rotates the tibia platform 3 relative to the stationary points $M_1$ and $M_2$ by an angle $\alpha_1$ in the direction towards the posterior about the point $M_1$. This displaced position is illustrated with phantom lines through a tibia platform 3' and its pivoted transversal plane 9'. At complete flexion of the condyles 1, 5 a torque acts in the opposite direction at the tibia and produces a rotational movement of the tibia platform 3 by an angle $\alpha_2$ about the point of rotation $M_1$. A tibia platform 3" which is correspondingly pivoted towards the anterior with its pivoted transversal plane 9" is shown in phantom lines. The medial plastic body 12 and the lateral meniscus part have flattenings 15 at their upper side which prevent unnecessarily high spherical sections from arising.

In FIG. 3 it is illustrated which movements the point $M_2$ of the meniscus part should make relative to the tibia platform 3 in order to fulfill the above-described function. The radius $R_5$ for the bulge 10 amounts to between 25 and 50 mm, for example 33 mm. The sum of the angles $\alpha_1+\alpha_2$ lies between 12° and 18°, for example at 15°.

Referring to FIG. 2, it is clear that the function of the knee prosthesis is maintained if a radius $R_1$, $R_2$ of one condyle 1, 5 is smaller than the radius $R_2$, $R_1$ of the other condyle 5, 1, respectively, by a specific amount and if the counter-surface A, B belonging to this smaller condyle projects further upwardly by this specific amount.

Figure 4:
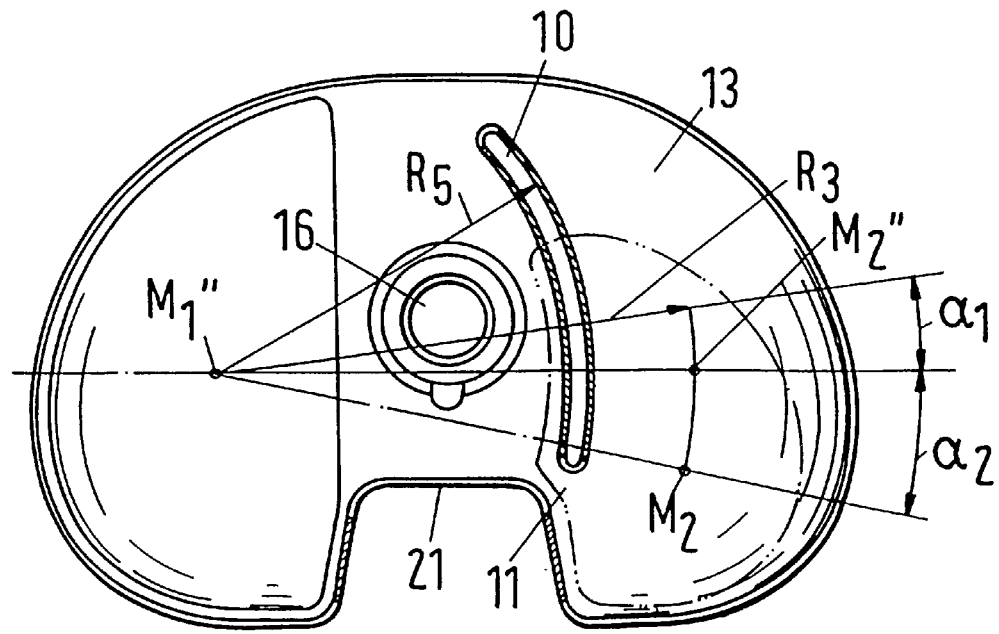
FIG. 4 shows analogously to FIG. 3 a tibia platform in asymmetrical design for a right knee.

The example of FIGS. 4 and 5 shows, an asymmetrical solution in which the medial side has a depression 19 for a plastic body 12, whereas the lateral side has a through-going planar guiding surface 13 from which a bulge 10 for the groove 11 of the meniscus part 7 protrudes. The kinematics of the pivotal movements between the tibia platform 3 and the meniscus part 7 are the same as in the example of FIGS. 1, 2 and 3.

A further constructional design is shown in the example of FIGS. 6 and 7; instead of circular guiding bulges, symmetrical medial and lateral depressions 19 can be provided in the form of a circular-arc-shaped groove 22 with lateral circular limitings through radii $R_4$ and $R_5$ in which a medial plastic body 12 is firmly anchored, whereas a lateral meniscus part 7 with its point $M_2$ is pivotal along the circular limitings around the point $M_1$ on a radius $R_3$ relative to the tibia platform. In FIG. 6 a flexion position is assumed in which the lateral meniscus part 7 is held in place unchanged by its condyle during the flexion, whereas the tibia platform 3 with its transversal plane 9 is pivoted from an initial position by an angle $\alpha_2$ into a transversal plane 9" towards the anterior. Abutments 23 limit the pivotal movement of the tibia platform 3 relative to the lateral meniscus part 7, which is shorter than the depression 19 in the direction of rotation.

Asymmetrical arrangements in which the medial depression 19 no longer represents a mirrored form of the lateral depression 19 can likewise be present in order to use the tibia platform at the right and at the left.

What is claimed is:

1. Knee prosthesis comprising a medial condyle having a running surface and a counter-surface (A) which lie on a tibia platform and which are sections of spherical surfaces with a radius ($R_1$), a center ($M_1'$), a vertical projection of which on the counter-surface (A) defining a point ($M_1$) which lies on an axis about which a lateral condyle can pivot, the lateral condyle comprising a running surface and a counter-surface (B) which are likewise sections of spherical surfaces with a radius ($R_2$) and a center ($M_2'$), a vertical projection of which on the counter-surface (B) defining a point ($M_2$); the counter-surface (B) belonging to an artificial meniscus part which can be displaced on a plane of the tibia platform and which, guided on a circular arc, is pivotal with the point ($M_2$) about the point ($M_1$) at a distance ($\alpha$) which corresponds to a distance a between the centers ($M_1'$, $M_2'$), the tibia platform being symmetrical with respect to its sagittal midplane in such a manner that each side is selectively suitable for receiving a firmly anchorable plastic body or a movable meniscus part in order to produce right and left tibia joint halves with one tibia platform.

2. Knee prosthesis in accordance with claim 1, wherein, when the meniscus part is held firmly, the tibia platform is pivotal by an angle $\alpha_1>0$ towards the posterior and by an angle $\alpha_2>\alpha_1$ towards the anterior about the axis from a middle position in which the points ($M_1$, $M_1'$; $M_2$, $M_2'$) lie in a transversal plane of the tibia platform.

3. Knee prosthesis in accordance with claim 2, wherein the angle $\alpha_2$ lies between 5° and 20°.

4. Knee prosthesis in accordance with claim 2, wherein the sum of the angles $\alpha_1$ and $\alpha_2$ lies between 12° and 18°.

5. Knee prosthesis in accordance with claim 1, including a circular-arc-shaped bulge on the tibia platform on an inner side of a lateral half of the tibia platform which engages a groove of the meniscus part for guiding the meniscus part.

6. Knee prosthesis in accordance with claim 5, wherein the bulge has an outer guiding surface corresponding to a radius ($R_5$) to the point ($M_1$); and wherein the radius ($R_5$) is between 25 mm and 50 mm.

7. Knee prosthesis in accordance with claim 1, wherein the counter-surface (A) is formed of a plastic body which is secured on the tibia platform; and wherein the meniscus part comprises plastic.

8. Knee prosthesis in accordance with claim 1, wherein the radius ($R_1$, $R_2$) of one condyle is smaller than the radius ($R_2$, $R_1$) of the other condyle by a specific amount; and wherein the counter-surface of the smaller condyle projects further upwardly by the specific amount.

9. Knee prosthesis in accordance with claim 1, including a circular-arc-shaped groove with an outer radius ($R_5$) and an inner radius ($R_4$) on a lateral side of the tibia platform.

10. Knee prosthesis in accordance with claim 9, wherein the tibia platform is symmetrical with respect to its midplane and includes first and second circular-arc-shaped grooves; and wherein an anchorable plastic body or a movable meniscus part of plastic is selectively available for the circular-arc-shaped groove.

11. Knee prosthesis comprising a medial condyle having a running surface and a counter-surface (A) which lie on a tibia platform and which are sections of spherical surfaces with a radius ($R_1$), a center ($M_1'$), a vertical projection of which on the counter-surface (A) defining a point ($M_1$) which lies on an axis about which a lateral condyle can pivot, the lateral condyle comprising a running surface and a counter-surface (B) which are likewise sections of spherical surfaces with a radius ($R_2$) and a center ($M_2'$), a vertical projection of which on the counter-surface (B) defining a point ($M_2$); the counter-surface (B) belonging to an artificial meniscus part which can be displaced on a plane of the tibia platform and which, guided on a circular arc, is pivotal with the point ($M_2$) about the point ($M_1$) at a distance ($\alpha$) which corresponds to a distance a between the centers ($M_1'$, $M_2'$), the tibia platform being symmetrical with respect to its sagittal midplane in such a manner that each side is selectively suitable for receiving a firmly anchorable plastic body or a movable meniscus part in order to produce right and left tibia joint halves with one tibia platform and a circular-arc-shaped bulge on the tibia platform on an inner side of a lateral half of the tibia platform which engages a groove of the meniscus part for guiding the meniscus part, the bulge having an outer guiding surface corresponding to a radius $R_5$ to the point $M_1$, the radius $R_5$ being between 25 mm and 50 mm.

* * * * *